(12) United States Patent
Walker

(10) Patent No.: US 11,517,526 B2
(45) Date of Patent: Dec. 6, 2022

(54) STABILISED HYPOCHLOROUS SOLUTIONS AND THEIR MEDICAL COSMETIC USES

(71) Applicant: Clinical Health Technologies Ltd, Hinckley (GB)

(72) Inventor: Ross Bedford Walker, Hinckley (GB)

(73) Assignee: Clinical Health Technologies Ltd.

( * ) Notice: Subject to any disclaimer, the term of this patent is extended or adjusted under 35 U.S.C. 154(b) by 0 days.

(21) Appl. No.: 17/434,731

(22) PCT Filed: Feb. 27, 2020

(86) PCT No.: PCT/IB2020/051683
§ 371 (c)(1),
(2) Date: Aug. 27, 2021

(87) PCT Pub. No.: WO2020/174436
PCT Pub. Date: Sep. 3, 2020

(65) Prior Publication Data
US 2022/0040101 A1 Feb. 10, 2022

(30) Foreign Application Priority Data

Feb. 28, 2019 (GB) ..................................... 1902731
Sep. 27, 2019 (GB) ..................................... 1913991

(51) Int. Cl.
| | |
|---|---|
| A61K 9/08 | (2006.01) |
| A61P 17/10 | (2006.01) |
| A61P 17/02 | (2006.01) |
| A61K 8/20 | (2006.01) |
| A61K 33/20 | (2006.01) |
| A61K 47/02 | (2006.01) |
| A61Q 11/00 | (2006.01) |
| A61Q 19/00 | (2006.01) |

(52) U.S. Cl.
CPC ................. *A61K 9/08* (2013.01); *A61K 8/20* (2013.01); *A61K 33/20* (2013.01); *A61K 47/02* (2013.01); *A61P 17/02* (2018.01); *A61P 17/10* (2018.01); *A61Q 11/00* (2013.01); *A61Q 19/00* (2013.01)

(58) Field of Classification Search
CPC ........ A61K 9/0014; A61K 33/20; A61K 8/20; A61K 9/0043; A61K 9/0053; A61K 47/02; A61K 9/08; A61K 2300/00; A61K 9/7007; A61Q 19/00; A61Q 11/00; A61P 17/10; A61P 17/02
See application file for complete search history.

(56) References Cited

U.S. PATENT DOCUMENTS

| | | | | |
|---|---|---|---|---|
| 2014/0134224 | A1* | 5/2014 | Mallet | A61L 2/0088 424/408 |
| 2015/0125551 | A1* | 5/2015 | Bond | A01N 59/00 424/665 |
| 2017/0266227 | A1 | 9/2017 | Almas | |

FOREIGN PATENT DOCUMENTS

| | | |
|---|---|---|
| GB | 2488838 A | 9/2012 |
| GB | 2521810 A | 7/2015 |
| JP | 2003052796 A | 2/2003 |
| WO | 10/148004 A1 | 12/2010 |
| WO | 12/0123695 A2 | 9/2012 |
| WO | 14/179692 A1 | 11/2014 |
| WO | 15/082937 A2 | 6/2015 |
| WO | 19/006217 A1 | 1/2019 |

OTHER PUBLICATIONS

English abstract for JP-2003052796.
Great Britain Combined Search and Examination Report dated Aug. 28, 2020 related to corresponding Great Britain Patent Application No. 2002779.3.
Wang et al. "Hypochlorous Acid as a Potential Wound Care Agent. Part 1 Stabilized Hypochlorous Acid: A Component of the Inorganic Armamentarium of Innate Immunity", Apr. 11, 2007.
Robson et al. "Hypochlorous Acid as a Potential Wound Care Agent. Part II Stabilized Hypochlorous Acid: Its Role in Decreasing Tissue Bacterial Bioburden and Overcoming the Inhibition of Infection on Wound Healing", Apr. 11, 2007.
Selkon, JB; et al. (2006). "Evaluation of hypochlorous add washes in the treatment of venous leg ulcers".

\* cited by examiner

*Primary Examiner* — Lezah Roberts
(74) *Attorney, Agent, or Firm* — Fishman Stewart PLLC

(57) ABSTRACT

A stabilised hypochlorous solution is disclosed. The solution includes hypochlorous acid (HOCl), hypochlorite (ClO—), and chlorine (Cl—) that combine to provide a total chlorine concentration. The total chlorine concentration is at or below 300 ppm, the hypochlorous acid, measured by UV spectroscopy at 230 nm, is the predominant species, the hypochlorite, measured by UV spectroscopy at 290 nm, is present at significantly lower levels than that of the hypochlorous acid, such that a ratio of hypochlorous acid to hypochlorite is greater than 7.5:1. The solution has a pH of between about 7 and 4 and a shelf life of at least 12 months, at 22° C., such that the amount of hypochlorous present remains at above 80% of its starting concentration, and the pH remains above 4.

20 Claims, 12 Drawing Sheets

FIG 3A

| Organism | Inoculum in 250ppm Product (cfu) | Log Reduction | % Reduction After Contact Time of 15 Seconds |
|---|---|---|---|
| Pseudomonas aeruginosa | $4.8 \times 10^6$ | >5.7 | 99.999% |
| Staphylococcus aureus | $4.7 \times 10^6$ | >5.7 | 99.999% |
| Escherichia coli | $5.0 \times 10^6$ | 5.2 | 99.999% |
| Enterococcus hirae | $3.6 \times 10^6$ | >5.6 | 99.999% |
| Acinetobacter baumannii | $2.4 \times 10^6$ | >5.4 | 99.999% |
| Enterococcus faecalis | $3.4 \times 10^6$ | >5.6 | 99.999% |
| MRSA | $5.3 \times 10^6$ | >5.7 | 99.999% |
| Staphylococcus epidermidis | $2.6 \times 10^6$ | >5.4 | 99.999% |
| Streptococcus pyogenes | $5.3 \times 10^6$ | >5.7 | 99.999% |
| Enterococcus faecium (VRE) | $1.1 \times 10^6$ | 5.0 | 99.999% |
| Listeria monocytogenes | $5.0 \times 10^6$ | >5.7 | 99.999% |
| Serratia marcescens | $6.9 \times 10^6$ | >5.8 | 99.999% |
| Proteus mirabilis | $3.9 \times 10^6$ | >5.6 | 99.999% |
| Candida albicans | $1.0 \times 10^6$ | >5 | 99.999% |
| Clostridium difficile | $1.3 \times 10^6$ | >4.1 | 99.99% |

14 of the 15 organisms tested showed a 99.999% reduction in microbial count after 15 seconds exposure to 250ppm.
14 of the pathogens still demonstrated a percentage reduction of 99.99% when exposed to 80ppm (data not shown)

FIG 3B

Blood

Enterovirus
Filoviridae
Flavivirus
Herpesviridae
Hepatitis A Virus (HAV)
Hepatitis B virus (HBV)

Hepatitis C virus (HCV)
Hepatitis Delta virus (HDV)
Human Immunodeficiency Virus (HIV)
Human T Cell Leukemia Virus (HTLV)
Parvovirus B 19

Respiratory tract

Adenovirus (Mast-)
Coronavirus
Enterovirus
Herpesviridae

Influenza Virus
Paramyxoviridae
Rhinovirus
Rubella Virus

Neural tissue, ear & nose, eye

Adenovirus (Mast-)
Enterovirus
Herpesviridae
Measles Virus

Human Immunodeficiency Virus (HIV)
Polyomavirus
Rabies Virus
Rubella Virus

Gastro-intestinal

Adenovirus (Mast-)
Caliciviridae
Coronavirus
Astrovirus

Enterovirus
Hepatitis A Virus (HAV)
Hepatitis E Virus (HEV)
Rotavirus

Skin, breast and/or milk

Enterovirus
Herpesviridae
Human Immunodeficiency Virus (HIV)

Human T Cell Leukemia Virus (HTLV)
Papillomavirus
Poxviridae

Spleen and lymph nodes (see also „Blood")

Human T Cell Leukemia Virus (HTLV)
Human Immunodeficiency Virus (HIV)

Dental procedure

Adenovirus (Mast-)
Enterovirus
Herpesviridae

Hepatitis C Virus (HCV)
Hepatitis Delta Virus (HDV)
Human Immunodeficiency Virus (HIV)

Hepatitis B virus (HBV)

FIG 3B (continued)

Urogenital tract

Hepatitis B Virus (HBV)
Herpesviridae
Human Immunodeficiency Virus (HIV)

Human T Cell Leukemia Virus (HTLV)
Papillomavirus
Polyomavirus

Day 1    Day 9

Stabilised hypochlorous solution applied 3 times per day

Stabilised hypochlorous solution applied to dressing 3 times a day for 10 days

|  | STRENGTH | ANTI-MICROBIAL | SPORICIDAL | NO RESISTANCE/ TOLERANCE CONCERNS | NON-IRRITANT TO SKIN, EYES, MUCUS MEMBRANES |
|---|---|---|---|---|---|
| 2% Chlorhexidine Gluconate | 20,000ppm | ✓ | ✗ | ✗ | ✗ |
| 20% Chlorhexidine Gluconate | 200,000ppm | ✓ | ✗ | ✗ | ✗ |
| 70% Alcohol | 700,000ppm | ✓ | ✗ | ✗ | ✗ |
| 10% Povidone Iodine | 100,000ppm | ✓ | ✗ | ✗ | ✗ |
| Stabilised hypochlorous solution | 250ppm | ✓ | ✓ | ✓ | ✓ |

FIG 9
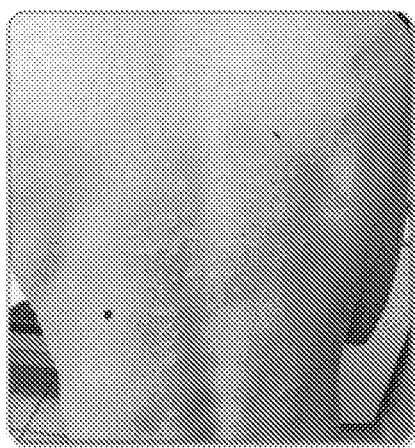
Stabilised hypochlorous solution applied following fall from ladder into stinging nettles
20 minutes after application
FIG 10
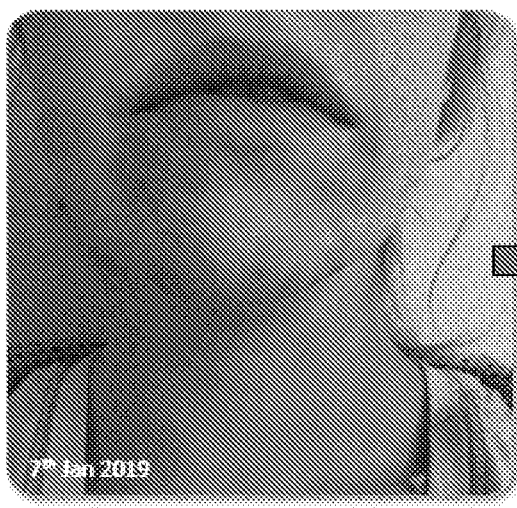

FIG 15A

Certificate of Analysis

Product:  Clinisept + Mouthwash          Production Date: 21/11/2018

Batch No.: 832609                         Approved Date: 22/11/2018

| Test | Specification limit | Method | Test Results |
|---|---|---|---|
| Appearance | Clear, colourless | Visual Check | Ok |
| pH | 5.5-7.5 | pH meter | 6.6 |
| Activity (as $Cl_2$) | 80 ppm ± 15% | Titrimetric | 83 |
| *Acitivity (as HOCl) | 53 ppm ± 15% | Calculated | 55 |
| Odour | Halogen odour | Odour check | Ok |

*Acitivity (as HOCl): an active chlorine level of 80ppm correlates to a hypochlorous acid concentration of 53 ppm ±15% based on average spectroscopy measurements on previous batches.

FIG 15B

Certificate of Analysis

Product:  Stabilised hypochlorous solution    Production Date: 21/11/2018

Batch No.: 832609                              Retest Date: 28/02/2019

| Test | Specification limit | Method | Test Results |
|---|---|---|---|
| Appearance | Clear, colourless | Visual Check | Ok |
| pH | 5.5-7.5 | pH meter | 6.5 |
| Activity (as $Cl_2$) | 80 ppm ± 15% | Titrimetric | 83 |
| *Acitivity (as HOCl) | 53 ppm ± 15% | Calculated | 55 |
| Odour | Halogen odour | Odour check | Ok |

*Acitivity (as HOCl): an active chlorine level of 80ppm correlates to a hypochlorous acid concentration of 53 ppm ±15% based on average spectroscopy measurements on previous batches.

STABILISED HYPOCHLOROUS SOLUTIONS AND THEIR MEDICAL COSMETIC USES

This application claims priority to International Patent Application No. PCT/IB2020/051683 filed Feb. 27, 2020, which claims priority to Great Britain Patent Application GB 1913991.4 filed Sep. 27, 2019 and Great Britain Patent Application GB 1902731.7 filed Feb. 28, 2019, the contents of each of which is hereby incorporated by reference in its entirety.

TECHNICAL FIELD

This invention relates to stabilised hypochlorous solutions and their medical and cosmetic uses. More particularly it relates to their use in the treatment of humans and animals by application to the skin, both external and internal surfaces, and more particularly, but not exclusively, to the treatment of wounds and the oral cavity. It also relates to its use in the tattoo industry and to applications as anti-viral targeting for example viruses as set out herein, including coronavirus.

BACKGROUND

The prior art discussed falls into two categories.

Generally, hypochlorous solutions are known to be effective anti-microbials. Indeed, as long ago as 1915, Alexis Carrel and Henry Dakin were championing its benefits.

However, a major problem with successful uptake is its poor shelf life because, in its natural state, hypochlorous has a half-life of 48 hours, unless stabilised.

WO2012123695 teaches a "stable" antimicrobial aqueous hypochlorous acid solution that retains its activity for at least three months and can be provided with high levels of hypochlorous acid (more than 500 ppm). The aqueous hypochlorous acid composition has low chloride ion concentrations (maximum chloride levels of 1:3 chloride to hydrochlorous acid) and a pH between 3.5 and 7.0.

The publication teaches the "stable compositions" (the activity of which in-fact varies with pH) may be used in a wide range of applications, the primary one exemplified being for sanitizing surfaces. It does however also teach its use in medicine to treat e.g. wounds, but no supporting evidence is provided, and no indication is given of the concentration of hypochlorous acid that may be required. Indeed, the general teaching is of a range of anywhere between 10 and 130,000 ppm, with the stability test data being with a solution containing 5000 ppm of "chlorine", apparently hypochlorous. This solution is still an order of magnitude higher than that contemplated with the hypochlorous solutions of the present invention which retain their high hypochlorous level over time.

GB2521810, which reference is incorporated by reference, teaches a method and apparatus for producing a stable acidic chlorinated solution having a pH between 3.0 and 6.5, a stability such that at 6 weeks storage at 20° C. the pH remains in the same range, and the amount of chlorine lost is less than 10%. Again, the general teaching focuses on a total chlorine content of 5000 ppm and the Example with the lowest chlorine concentration exceeds 1000 ppm. It's states its use in disinfection and in the chlorination of water. The chlorine dissolves in water to produce hypochlorous acid, hydrogen ions and chloride ions and the hypochlorous dissociates to produce hydrogen ions and hypochlorite ions.

The medical uses of hypochlorous are known per se. Hypochlorous acid has been investigated as a possible wound care agent and as of early 2016 the U.S. Food and Drug Administration has approved products whose main active ingredient is hypochlorous acid for use in treating wounds and various infections in humans and pets.

The referenced publications are:

Wang L et al. "Hypochlorous acid as a potential wound care agent. Part I Stabilized hypochlorous acid: a component of the inorganic armamentarium of innate immunity". *J Burns and Wounds* 2007; April: 65-79. This document discloses stabilized HOCl in the form of a physiologically balanced solution in 0.9% saline, at a pH range of 3.5 to 4.0. Chlorine species distribution in solution is a function of pH. In aqueous solution, HOCl is the predominant species at the pH range of 3 to 6. At pH values less than 3.5, the solution exists as a mixture of chlorine in aqueous phase, chlorine gas, trichloride ($Cl_3$—), and HOCl. At pH greater than 5.5, sodium hypochlorite (NaOCl) starts to form and becomes the predominant species in the alkaline pH. To maintain HOCl solution in a stable form, maximize its antimicrobial activities, and minimize undesirable side products, the pH must be maintained at 3.5 to 5.

Robson M C et al. "Hypochlorous acid as a potential wound care agent. Part II Stabilized hypochlorous acid: its role in decreasing tissue bacterial bioburden and overcoming the inhibition of infection on wound healing". *Journal of Burns and Wounds* 2007; April: 80-90. This document teaches stabilized hypochlorous acid (NVC-101) prepared by the addition of sodium hypochlorite to a solution of sodium chloride in sterile water followed by addition of a solution of hydrochloric acid and maintained at a pH between 3.5 and 5 has been demonstrated to have excellent in vitro antibacterial properties. Its potential limitation is the requirement to maintain its narrow pH range in the clinical wound environment.

Selkon, J B; et al. (2006). "Evaluation of hypochlorous acid washes in the treatment of venous leg ulcers". J Wound Care. 2006 (15): 33-37. This document teaches the production of hypochlorous in situ, at a pH of 5.4 to 5.8.

A problem with the medical application of hypochlorous solutions, unlike general sanitation, is the need for consistency and accuracy of product with a shelf life of at least 3 months and preferably longer. It is also desirable for it to have a reasonable life once opened. Applicant has worked with solutions manufactured according to the process described in GB2521810 but rather they produce much lower concentrations of total chlorine by careful (stoichiometric) control of the reactants: water, hypochlorite salt (typically a sodium or calcium salt), and acid (typically phosphoric acid). This results in a relatively low total chlorine content (below 500 ppm) but very importantly a high, predominant, concentration of hypochlorous, and a ratio of hypochlorous to hypochlorite of greater than 3:1 and more preferably much higher which distinguishes it from prior art solutions. This high ratio of hypochlorous to hypochlorite, coupled with the relatively low total chlorine makes them particularly suitable for medical applications where the solution is applied to the skin or wounds of humans or animals. This coupled to higher pH's make it possible to use bottled hypochlorous solutions rather than seeking to produce hypochlorous in situ.

As described in GB2521810 the reaction utilises:
i) a source of water having an electrical conductivity of no more than 500 $\mu Scm-1$ at 20° C.;
ii) a high (greater than 60% pure) purity hypochlorite salt, such as calcium hypochlorite (the sodium salt may also be used); and
iii) an acid to adjust the pH to between 3.0 and 6.5.

The water is a "de-ionised water" with a minimal chlorine content and a defined conductivity.

Preferably the water has been subject to a reverse osmosis process and a "polishing" process using a mixed bed ion exchange resin wherein residual ions (such as chloride ions) are exchanged for H$^+$ and OH$^-$ ions.

It may additionally have been treated to kill microbes, using electromagnetic radiation, such as ultra-violet (UV) radiation and filtered through a filter, such as a 1 micron filter.

The hypochlorite salt may be calcium hypochlorite, with a purity level of at least 60% pure (by weight) and a low chloride content.

The, for example, calcium hypochlorite is mixed in the appropriate stoichiometric amount with the water to produce the desired concentration and the pH controlled with e.g. phosphoric acid, with the precipitate being removed by e.g. filtration.

Alternatively, the salt may be a high purity sodium hypochlorite.

Hydrochloric acid should not be used because it is a source of chloride ions which will negatively impact the stability of the final product.

These solutions of the invention, with a defined hypochlorous concentration (in ppm) and having a high ratio of hypochlorous to hypochlorite, have been demonstrated to have good shelf life and good efficacy overcoming many of the issues faced by hypochlorous products currently available which also contain relatively high hypochlorite levels.

Therapeutically this is very significant since the hypochlorous is much more efficacious and non-toxic whereas the hypochlorite is more than a log fold less efficacious and is toxic in nature.

The Applicant has further tested two preferred, low concentration, solutions in clinical settings and found them to be highly effective in promoting cell regeneration as well as acting as antimicrobials, including being highly effective against viruses including corona virus.

In the field of dentistry and oral hygiene the gold standard treatments comprise chlorohexidine gluconate. These mouthwashes can irritate ulcers and mucus membranes. Furthermore, they may cause staining, allergic reactions and do nothing to promote cell regeneration. Microbes can also become resistant to chlorhexidine.

Alternative antimicrobials used in medicine include isopropyl alcohol and povidone iodine.

They have also tested the product as a cosmetic, as a product for use in the tattoo industry with impressive results compared to the use of "green soap" the standard product used in the industry.

At first sight it may appear to the uninitiated that one hypochlorous solution will be much like another. However, as is apparent from observations made in prior art solutions Applicants ability to produce a stable hypochlorous solution with a high ratio of hypochlorous to hypochlorite (greater than 3:1) is a very significant industry development Thus, for example US2017/0266227, FIG. 10, illustrates even the best "reagent grade" hypochlorous loses a third of its active hypochlorous in 12 weeks and will have halved (by extrapolation) in less than 18 weeks. Such compositions, as illustrated by for example, applicant's comparative example—see FIG. 4A, do not have the high hypochlorous: hypochlorite ratio that Applicants product has ensuring its superior efficacy.

Similarly, it will be noted that in WO2015/061632, page 2, paragraph 2, it is acknowledged that an aqueous HOCl solution at pH 4-6 in which the HOCl is the predominant active species is an effective topical disinfectant, However, the very next paragraph goes on to explain the difficulties and limitations in storage are a major problem. Indeed the specification uses terms such as "the remarkable difficulty of storing them" has led to the creation of machinery to generate such solutions in situ. Whilst the Examples are stated to produce specified concentrations of hypochlorous (100 and 500 ppm) of low chlorine content (less than 5 ppm) but of undefined hypochlorite. What is taught in the Examples is that various phosphates are added in the manufacture and US2017/0266227 teaches that surprisingly a phosphate buffer negatively impacts on the hypochlorous as illustrated in FIG. 10 therein Other art identified with similar limitations include JP2003052796 which is acidified with HCl and includes phosphoric acid WO2019006217 which appears to be no more than a description of desire with no specific teaching of processes used to obtain the disclosed formulations which are silent on their content other than a hypochlorous content; and JP2003/052796, which is acidified with HCl,

SUMMARY

In accordance with the present inventions there is provided a bottle or an otherwise contained stabilised hypochlorous solution comprising:

hypochlorous acid (HOCl), hypochlorite (ClO$^-$), and chlorine (Cl$^-$), which species combined provide a total chlorine concentration, characterised in that;

the total chlorine concentration is at or below 300 ppm;

the hypochlorous, measured by UV spectroscopy at 230 nm, is the predominant species;

the hypochlorite, measured by UV spectroscopy at 290 nm, is present at significantly lower levels than that of the hypochlorous, such that ratio of hypochlorous acid to hypochlorite of greater than 3:1; and the solution has a pH of between about 7 and 4 and has a shelf life of at least 3 months, at 22° C., such that the amount of hypochlorous present remains at above 50% of its starting concentration, and the pH remains above 3.5.

In a preferred embodiment the solution has a shelf life, at 22° C., of at least 6 months, more preferably at least 9 months through 12 months, 15 months, 18 months, 21 months to 24 months or more.

Most preferably, at each of these time intervals the amount of hypochlorous present remains at above 60% through 65%, 70%, 75%, 80%, 85% and 90%.

In addition to good shelf life (period of storage) it is important that the product has a once open life, at 22° C., of at least 2 weeks and preferably at least 4 weeks, such that the amount of hypochlorous present remains at above 80% of its concentration before opening.

For a solution with a chlorine content of about 250 ppm this can be 3 months, and for a product with a chlorine content of about 80 ppm this should be at least 4 weeks.

In the solutions of the invention the ratio of hypochlorous to hypochlorite remains Greater than 3:1, more preferably greater than, 4:1 through each of 5:1, 6:1, 7:1, 8:1 or more during storage.

Preferably the pH remains at above 5, more preferably above 4.5, through 4 to above at least 3.5.

Most preferably the ratio of hypochlorous to hypochlorite is greater than 3:1, more preferably still greater than 5:1, through 7.5:1 to greater than 9:1. The ratio is generally higher for the about 250 ppm product than the about 80 ppm product.

In a first, preferred, embodiment the contained stabilised hypochlorous solution has a total chlorine concentration of about 250 ppm+/−20% with a starting concentration of hypochlorous of between 120 and 160 ppm.

This embodiment has been demonstrated to be particularly effective in treating a number of medical conditions including wounds, particularly chronic wounds, such as, for example, ulcers, as well as burns, urticaria as well as in the treatment of acne, spots and pimples.

It has further proved effective in cosmetic applications and in tattoo care reducing redness, swelling and pain during tattooing, (enabling the artist to work longer on a subject) when applied before and during the tattooing procedure, as well as speeding healing times. It further improved colour retention.

It may also be used pre, during and post tattoo removal. The tattoo removal process may be a laser process or by micro-needling.

The hypochlorous solution of the invention has also been shown to be very effective against viruses including corona virus.

It has also been demonstrated to have a shelf life of up to 2 years and a once open life of up to 3 months, retaining its relative hypochlorous levels and a high ratio of hypochlorous to hypochlorite which contributes significantly to its medical activity.

In a second, preferred, embodiment, and one particularly suited for dental applications and oral hygiene there is provided a contained stabilised hypochlorous solution which has a total chlorine concentration of about 80 ppm+/−20% and the starting concentration of the hypochlorous is above 40 ppm and more preferably above 50 ppm to about 55 pppm.

In accordance with a second aspect of the present invention there is provided the contained stabilised hypochlorous solution of the first preferred embodiment for use in the treatment of a number of medical conditions including wounds, particularly chronic wounds, such as, for example ulcers, as well as burns, urticaria as well as in the treatment of acne, spots and pimples.

In accordance with a third aspect of the present invention there is provided the contained stabilised hypochlorous solution of the second preferred embodiment for use in the treatment of dental and/or oral hygiene diseases and conditions including, but not limited to implants, extractions, dental caries, periodontitis, lichen planus, implantitis, gingivitis, mucosal bleeding, ulcers, bad breath, gum health and excess plaque.

The solution used in this aspect typically takes the form of a mouthwash.

The "contained" solution is contained in a bottle or other suitable container. The container should be impervious to light and may comprise a measuring aid or spray delivery device in order to facilitate easy application.

In accordance with a fourth aspect of the present invention there is provided a method of treating a subject for a condition selected from treatment of wounds, burns, the oral cavity, urticaria or acne, spots or pimples, comprising administering a contained stabilised hypochlorous solution to the subject.

The solution may be administered directly or applied to, for example a dressing, bandage, gauze or the like.

In accordance with a fifth aspect of the present invention there is provided a stabilised hypochlorous solution of the first or second aspect of the invention for use in treating a viral respiratory infection.

In one embodiment the viral respiratory infection is a corona virus infection. More particularly it is caused by COVID-19.

In accordance with a sixth aspect of the present invention there is provided a method of treating a viral respiratory infection comprising applying a stabilised hypochlorous solution of the first or second aspect of the invention to a subject.

In a preferred embodiment the solution is applied to the skin externally.

In another embodiment it is applied internally. It may be delivered to the oral cavity as a spray or as a liquid or the lungs as a spray or nebuliser. It may also be delivered to the lungs nasally.

BRIEF DESCRIPTION OF THE DRAWINGS

Embodiments of the invention are further described hereinafter with reference to the accompanying drawings, in which:

FIG. 3a is an illustration of the effect of two different concentrations of the hypochlorous solution of the invention on a range of microbes;

FIG. 3b illustrates the effect on viruses, including corona virus;

FIG. 9 illustrates the effect of the hypochlorous solution (250 ppm) of the invention in skin calming;

FIG. 10 illustrates the effect of the hypochlorous solution (250 ppm) of the invention on acne;

FIGS. 15a and 15b are certificates of analysis for the solution (80 ppm) of the invention at time zero and 3 months, demonstrating retained stability;

DETAILED DESCRIPTION

Referring to the figures, two formulations of the invention (about 250 ppm and about 80 ppm total chlorine) have been investigated in medicine. The term "about" is intended to provide for a +/−20% variation.

The first is a hypochlorous solution which has been tested in a range of settings including: piercing and aesthetics, as a skin cleanser, and then at a total chlorine concentration of 250 ppm (hypochlorous concentration of about 150 ppm) as a wound healing treatment in a range of conditions including: burns, ulcers, for the treatment of urticaria and in the treatment of acne, spots and pimples which may be medical or cosmetic in nature.

The second is a hypochlorous solution at a lower total chlorine concentration, 80 ppm (hypochlorous concentration of about 55 ppm), where it has been tested in a range of dentistry situations ranging from extractions, implants, dental caries, post treatment care, ulcers, mucosal bleeding, periodontis, lichen planus, implantis, gingivitis and poor oral hygiene, were it has been benchmarked against typical standard of care alternatives such as chlorhexidine gluconate.

Figure 1:
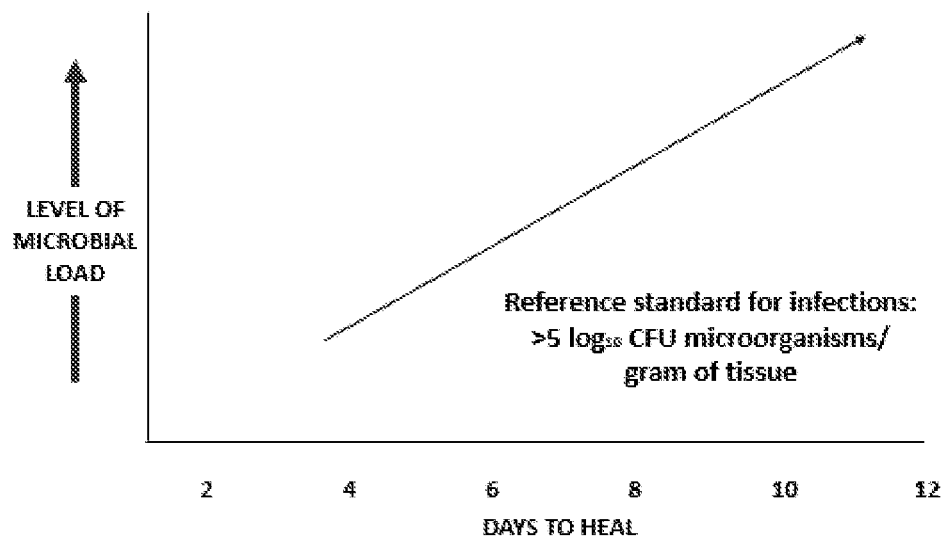
FIG. 1 is a graph showing the impact of microbial load on speed of healing.

FIG. 1 illustrates that the speed at which a wound heals is proportional to microbial load. Therefore, before conducting a procedure, such as, ear piercing or an aesthetic procedure, it is good practice to clean the skin to reduce microbial load.

Figure 2:
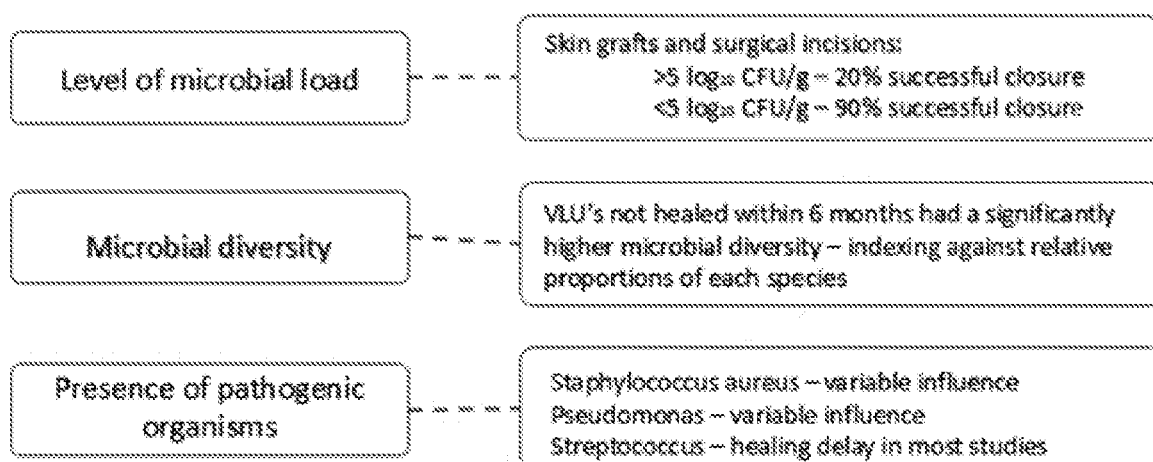
FIG. 2 is an illustration of three microbial variables which impact on wound closure.

In fact, as illustrated in FIG. 2a, the success of healing post incision changes dramatically with the log count of microbes, with the colony forming unit (CFU) figure of $10^5$ per ml or g being the tipping point between the chance of 90% closure (below) or 20% closure success (above).

Other significant factors include the diversity of microorganisms, and the presence or absence of, particularly, streptococcus. Thus, an active with wide ranging microbial action is desirable and FIGS. 3A and 3B illustrate the fact that the hypochlorous solution of the invention at 250 ppm reduced the count of a wide range of organisms by over 99.9%, and in fact over 99.99% or more, with a contact time of as little as 15 seconds.

Perhaps more surprisingly, even at 80 ppm a 99.99% reduction was achieved against 14 of the 15 organisms tested in FIG. 3a FIG. 3b is a modified vaccina virus Ankara test report conducted according to EN 14476:2013+A1:2015. Again, it demonstrates a 4 $\log_{10}$ reduction in viral activity (greater than 99.99% inactivation) for the viruses identified on a 15 second exposure. Enveloped viruses are identified in bold.

Figure 4A:
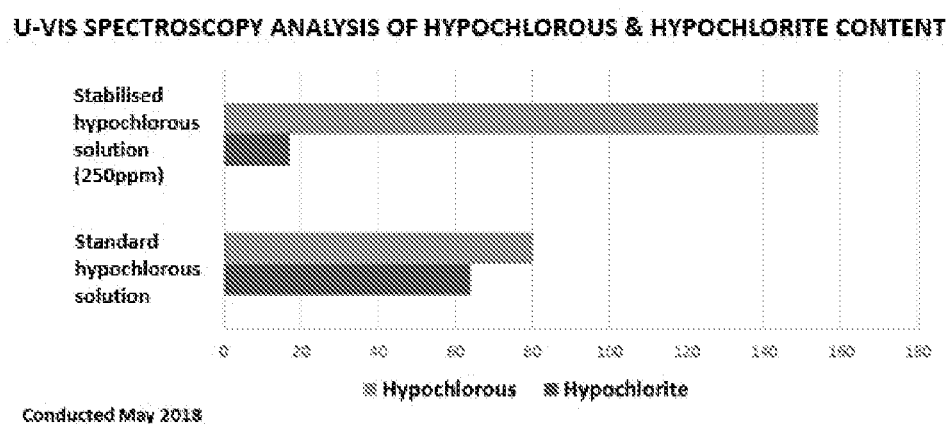
FIGS. 4a and 4b are graphs illustrating the significant difference in the hypochlorous: hypochlorite ratio of Applicant's stabilised hypochlorous solution, compared to a typical hypochlorous solutions of the art (produced by electrolysis and chemically stabilised) at an interval of 8 months.
Figure 4B:
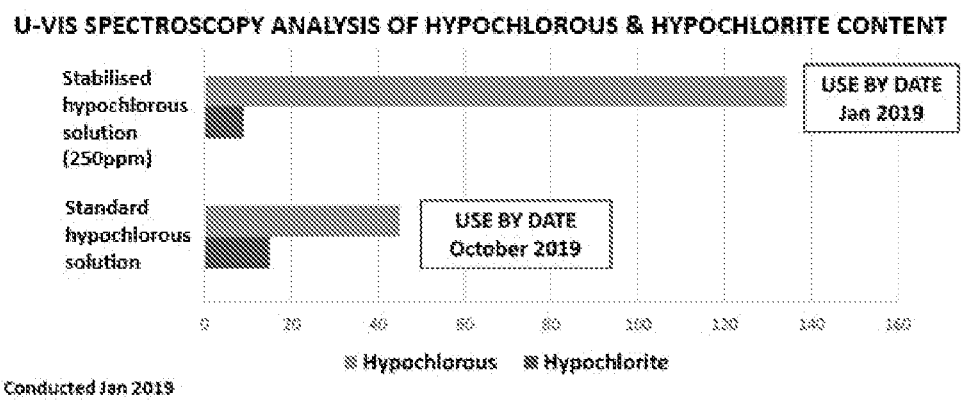

These remarkable figures come down to the high initial concentration of hypochlorous relative to hypochlorite (FIG. 4a), (greater than 3:1) and the stability of the hypochlorous over time (FIG. 4b). Both FIGS. 4a and 4b provide a UV spectroscopy analysis of the relative concentration of hypochlorous and hypochlorite in applicant's product compared to a conventional hypochlorous solution. Its will be apparent from FIG. 4a that the ratio of hypochlorous to hypochlorite is very approximately 150:15 (10:1) for the (250 ppm) solution of the invention compared to very approximately 80:65 (1.25:1) for the comparator. This is highly significant because hypochlorous acid (HOCl) is 80-100 times more effective as an antimicrobial than hypochlorite (OCl$^-$). More significantly both the ratio of hypochlorous to hypochlorite and the amounts are maintained over approx. 9 months.

The challenge is perhaps well illustrated by Table 1 below, which illustrates how bleach disassociates with pH.

TABLE 1

| Free Cl2 ppm | pH | % HOCl | % OCl |
|---|---|---|---|
| 100 | 7.83 | 30% | 70% |
| 200 | 8.33 | 10% | 90% |
| 500 | 8.73 | 5% | 95% |
| 1000 | 9.24 | 3% | 97% |
| 2000 | 9.57 | 2% | 98% |

In other words, as pH increases so the relative proportions of hypochlorous decrease.

Applicants product is differentiated from products produced by e.g. electrolysis or less well stabilised chemistry based on the unprecedented high proportion of hypochlorous to hypochlorite and an initial pH of between 5 and 7. They demonstrate high efficacy at what would be considered relatively low doses of total chlorine, less than 500 ppm.

The beneficial effects of treatment with these solutions is illustrated in Examples 1 to 7 which utilise, respectively, solutions manufactured in accordance with the methodology of GB2521810 but producing much lower concentrations of total chlorine by careful control of the reactants: water, hypochlorite salt (typically the calcium or sodium salt), and acid. This results in a relatively low total chlorine content (below 500 ppm) but a high, predominant, concentration of hypochlorous, and a ratio of hypochlorous to hypochlorite of greater than 3:1 and often much higher (dependent on total chlorine concentration.)

A high purity hypochlorite salt, typically calcium or sodium, is stoichiometrically reacted with water having an electrical conductivity of no more than 500 μScm-1 at 20° C., and a pH controlling agent, typically phosphoric acid, and any phosphate precipitate (sodium or calcium phosphate) is removed by filtration. The initial pH is adjusted to be about pH 7.

Example 1

Figure 5:
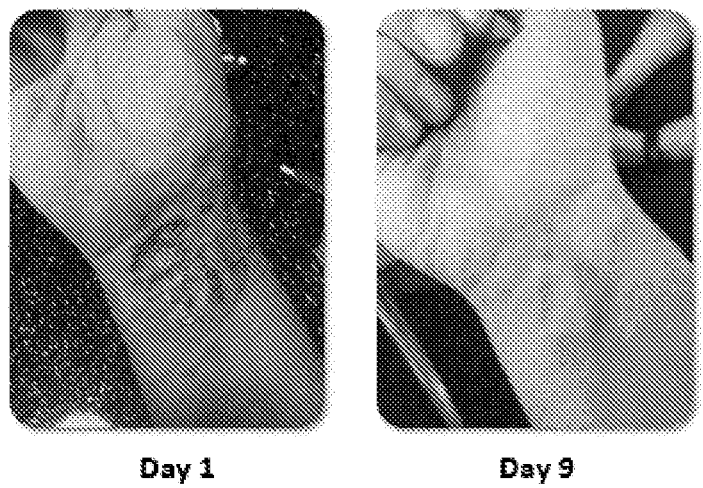
FIG. 5 illustrates the effect of the hypochlorous solution (250 ppm) of the invention in healing burns.

A patient with a burn wound, from a deep fat fryer, was treated with a 250 ppm stabilised hypochlorous solution of the invention following blister bursting. The solution was applied 3 times daily. The wound was fully healed at day 9. The results are illustrated in FIG. 5.

Example 2

Figure 6:
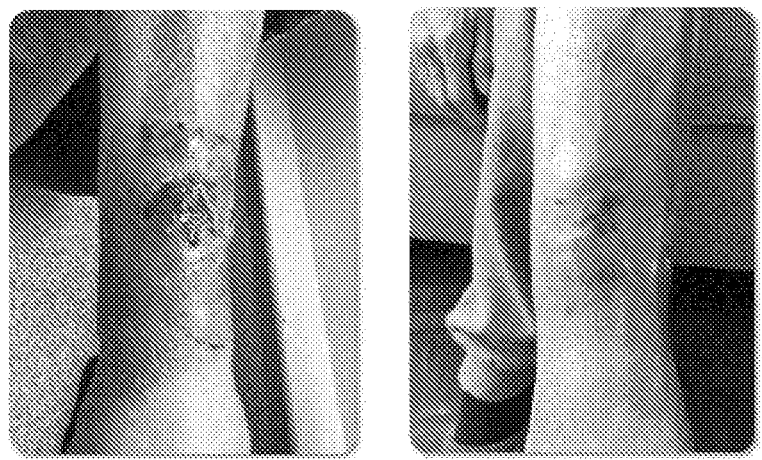
FIG. 6 illustrates the effect of the hypochlorous solution (250 ppm) of the invention in healing ulcers.

A patient with what is termed a "chronic wound", a non-healing ulcer, was treated with a 250 ppm stabilised hypochlorous solution, by its application onto a dressing, which was applied 3 times a day. The ulcer was fully healed at day 10. The results are illustrated in FIG. 6.

Example 3

A patient with a sore persisting bleeding mucosa (treated with steroids) was given a mouthwash comprising an 80 ppm stabilised hypochlorous solution of the invention. They gargled with it once per day for 2 weeks. The results are illustrated in FIG. 7.

Figures 7, 8:
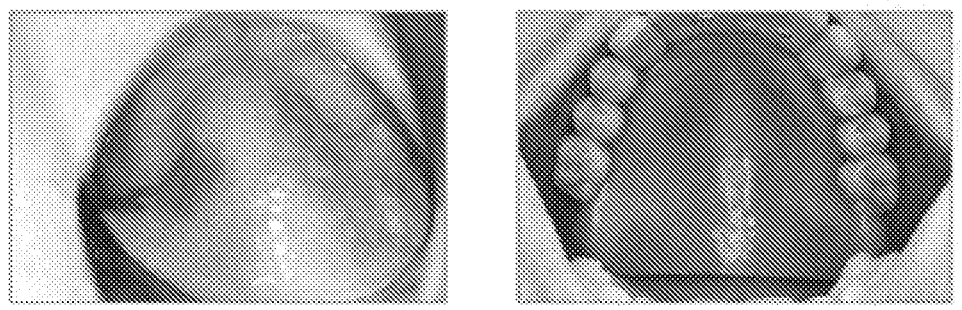
FIG. 7 illustrates the effect of the hypochlorous solution of the invention (80 ppm) in oral hygiene.
FIG. 8 is a Table comparing the hypochlorous solution of the invention (at 250 ppm) with skin disinfectants of the art.

That such a low concentration (total chlorine) dose is highly effective was surprising and compares highly favourably to traditional standards of care medications used in the dental industry as illustrated in FIG. 8, which in contrast to Example 3, was conducted with a 250 ppm hypochlorous solution.

Example 4

A patient who had fallen from a ladder into a bed of stinging nettles was treated with 250 ppm stabilised hypochlorous solution of the invention. 20 minutes post treatment the inflammation has significantly reduced as illustrated in FIG. 9 and the stinging ceased.

Example 5

A patient presenting with acne used the 250 ppm stabilised hypochlorous solution of the invention daily for 5 days and the improvement is illustrated in FIG. 10.

From the clinical Examples, and comparative data, it will be apparent that the solutions of the invention are acting in a highly effective manner.

The stability of the respective formulations is illustrated in FIGS. 11 to 15.

Figure 11:
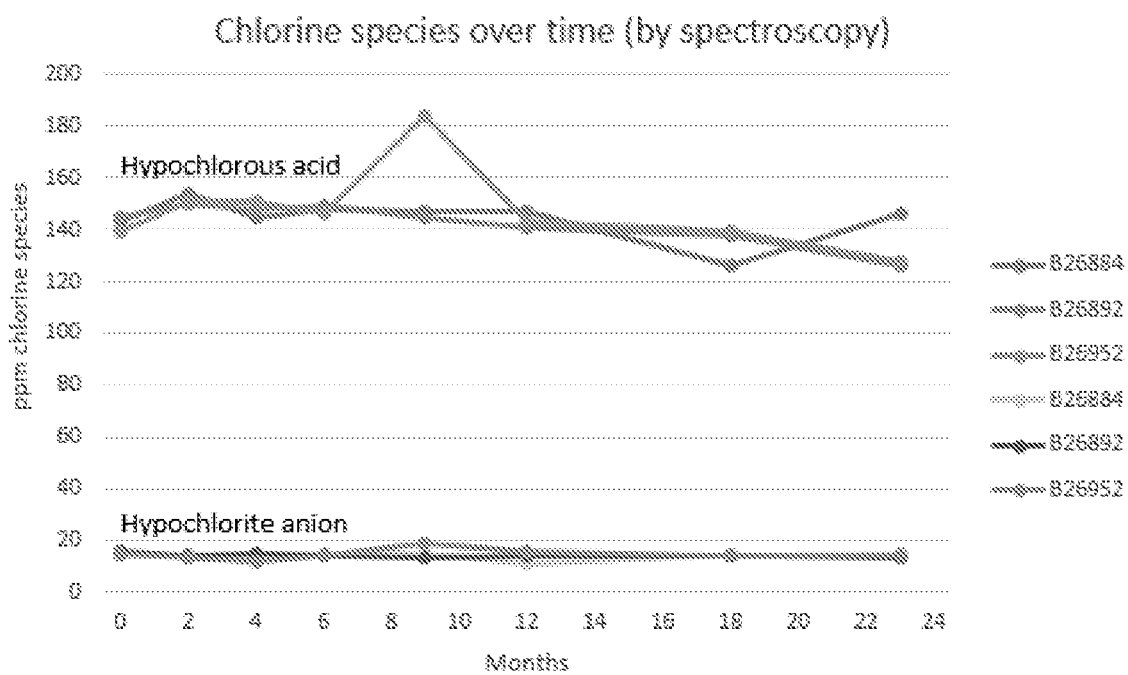
FIG. 11 shows the stability of the hypochlorous: hypochlorite ratio of the solution (250 ppm) of the invention over 24 months.

FIG. 11 shows the stability of the hypochlorous: hypochlorite ratio of the solution (250 ppm) of the invention generally remains constant with the hypochlorous level remaining between 120 and 160 ppm over 24 months, with the much lower hypochlorite levels also remaining constant.

Figure 12:
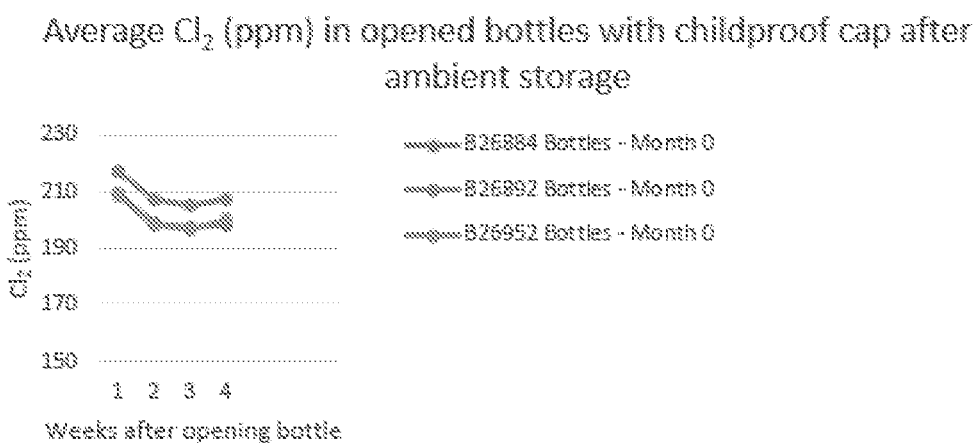
FIG. 12 shows the change in total chlorine concentration of the solution (250 ppm) of the invention at 22° C. over 4 weeks from opening.

FIG. 12 shows that even after opening the solution retains its total chlorine levels over a 4 weeks period.

Figure 13:
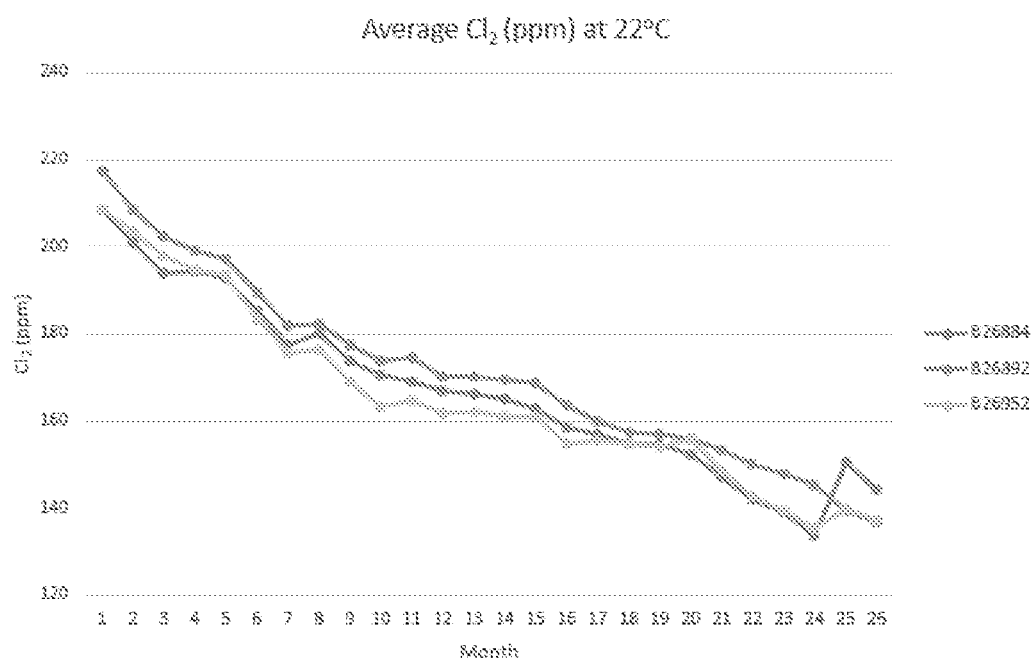
FIG. 13 shows the change in total chlorine concentration of the solution (250 ppm) of the invention at 22° C. over 24 months.

FIG. 13 shows the change in total chlorine concentration of the solution (250 ppm) of the invention at 22° C. over 24 months. Over 6 months the total concentration remains at about 90% of the starting level, staying at over 80% for 12 months and over about 70% for up to 24 months.

Figure 14:
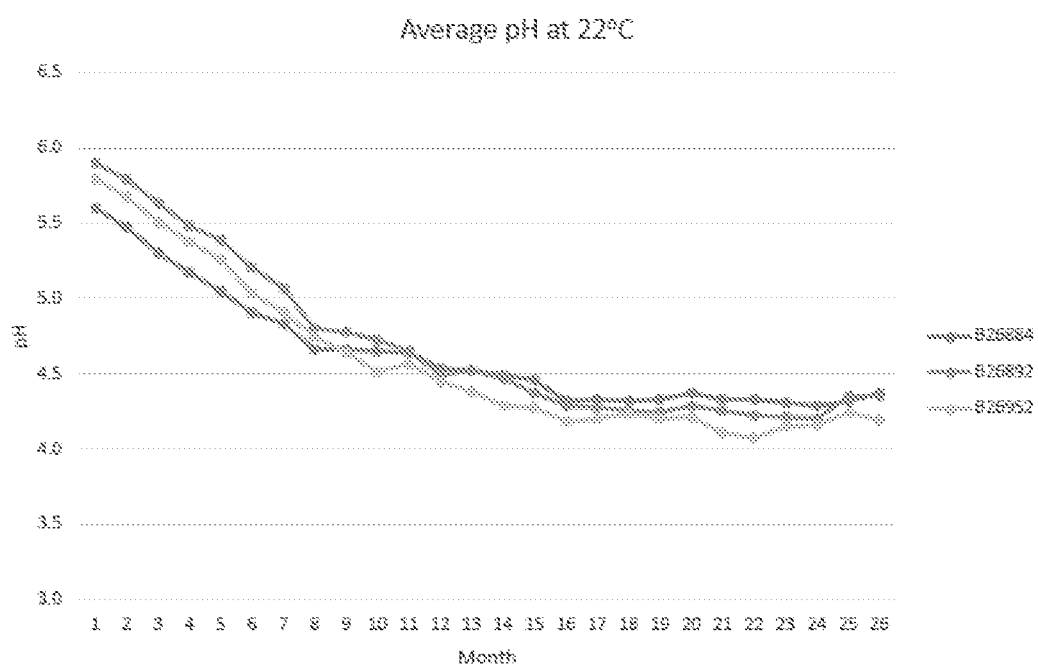
FIG. 14 shows the change in pH of the solution (250 ppm) of the invention at 22° C. over 24 months.

FIG. 14 shows the change in pH of the solution (250 ppm) of the invention at 22° C. over 24 months. It stays above 5 for 6 months and above 4 over 24 months.

Finally, FIGS. 15*a* and 15*b* are certificates of analysis of the about 80 ppm solution of the invention at bottling and 3 months later. The striking feature of note is that the hypochlorous levels remain constant (greater than 90%) over time.

Example 6

Figure 16:
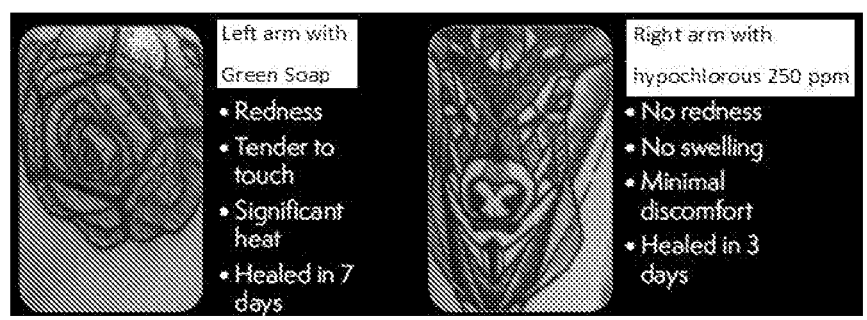
FIG. 16 illustrates the difference in performance between the use of green soap applied pre and during tattooing and the hypochlorous solution (250 ppm) when applied pre, during and post tattooing.

A subject having tattoos applied to their left and right arms were treated with respectively, "green soap" on the left arm and a hypochlorous solution (250 ppm) of the invention on the right arm. The skin was wiped pre commencement of tattooing and during the tattooing process with the respective solutions. Post the tattooing the hypochlorous solution was applied 3 times a day. The results (tattoo appearance) are illustrated in FIG. 16 together with the bulleted findings. The use of the hypochlorous proved beneficial in a number of significant ways which also included a higher quality tattoo (better colouring and definition), Example 7

Figure 17:
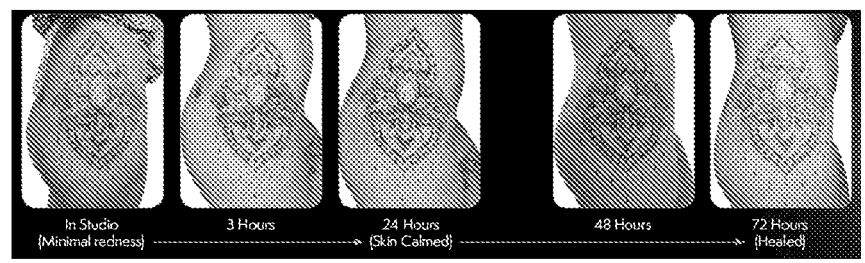
FIG. 17 illustrates the effects of the hypochlorous solution (250 ppm) over a 72-hour period having been applied pre, during and post tattooing

A subject having a tattoo was followed and photographed immediately post having a tattoo applied and was followed and photographed at regular intervals over a 72-hour period. The results are illustrated in FIG. 17. All the benefits identified in Example 6 were experienced in this Example too.

The invention claimed is:

1. A stabilised hypochlorous solution contained in a bottle impervious to light, comprising:
   hypochlorous acid (HOCl),
   hypochlorite (ClO—), and
   chlorine (Cl—),
   which species combined provide a total chlorine concentration,
   wherein the stabilised hypochlorous solution is obtained by stochiometric control of reactants water, calcium or sodium hypochlorite salt and phosphoric acid utilising:
   i) a source of de-ionised water having an electrical conductivity of no more than 50 μScm−1 at 20° C.;
   ii) a greater than 60% pure calcium or sodium hypochlorite salt; and
   iii) phosphoric acid;
   the total chlorine concentration is at or below 300 ppm;
   the hypochlorous acid, measured by UV spectroscopy at 230 nm, is the predominant species;
   the hypochlorite, measured by UV spectroscopy at 290 nm, is present at lower levels than that of the hypochlorous acid, such that a ratio of hypochlorous acid to hypochlorite is greater than 7.5:1, and
   the solution has a pH of between about 7 and 4 and a shelf life of at least 12 months, at 22° C., such that the amount of hypochlorous present remains at above 80% of its starting concentration, and the pH remains above 4.

2. A stabilised hypochlorous solution as claimed in claim 1, which has a once open life of at least 4 weeks, at 22° C., such that the amount of hypochlorous present remains at above 80% of its concentration before opening.

3. A stabilised hypochlorous solution as claimed in claim 1, wherein the ratio of hypochlorous acid to hypochlorite is greater than 9:1.

4. A stabilised hypochlorous solution as claimed in claim 1, wherein the total chlorine concentration is 250 ppm +/−20% and the starting concentration of the hypochlorous is between 120 and 160 ppm.

5. A stabilised hypochlorous solution as claimed in claim 1, wherein the total chlorine concentration is 80 ppm +/−20% and the starting concentration of the hypochlorous is above 40 ppm.

6. A stabilised hypochlorous solution as claimed in claim 1, for use in wound healing.

7. A stabilised hypochlorous solution as claimed in claim 6, wherein the wound is a chronic wound.

8. A stabilised hypochlorous solution as claimed in claim 7, wherein the chronic wound is an ulcer or a burn.

9. A stabilised hypochlorous solution as claimed in claim 1, wherein the hypochlorite salt is sodium hypochlorite.

10. A stabilised hypochlorous solution as claimed in claim 1, for use in the treatment of urticaria.

11. A stabilised hypochlorous solution as claimed in claim 1, for use in the treatment of acne, spots, pimples and the like.

12. A stabilised hypochlorous solution as claimed in claim 1, for use at least one of before, during and after tattooing.

13. A stabilised hypochlorous solution as claimed in claim 5, for use in dentistry.

14. A stabilised hypochlorous solution as claimed in claim 1, which is packaged for delivery as a nebuliser or nasally.

15. A method of treating a subject for a condition selected from treatment of wounds, burns, the oral cavity, urticaria or acne, sports or pimples comprising:
   administering a contained stabilised hypochlorous solution from a bottle impervious to light to the subject, the contained stabilised hypochlorous solution including:

hypochlorous acid (HOCl),
hypochlorite (ClO—), and
chlorine (Cl—),
which species combined provide a total chlorine concentration,
wherein the stabilised hypochlorous solution is obtained by stochiometric control of reactants water, calcium or sodium hypochlorite salt and phosphoric acid utilising:
i) a source of de-ionised water having an electrical conductivity of no more than 50 μScm−1 at 20° C.;
ii) a greater than 60% pure calcium or sodium hypochlorite salt; and
iii) phosphoric acid;
the total chlorine concentration is at or below 300 ppm;
the hypochlorous acid, measured by UV spectroscopy at 230 nm, is the predominant species;
the hypochlorite, measured by UV spectroscopy at 290 nm, is present at significantly lower levels than that of the hypochlorous acid, such that a ratio of hypochlorous acid to hypochlorite is greater than 7.5:1, and the solution has a pH of between about 7 and 4 and a shelf life of at least 12 months, at 22° C., such that the amount of hypochlorous present remains at above 80% of its starting concentration, and the pH remains above 4.

16. A method as claimed in claim 15, which has a once open life of at least 4 weeks, at 22° C., such that the amount of hypochlorous present remains at above 80% of its concentration before opening.

17. A method as claimed in claim 15, wherein the ratio of hypochlorous acid to hypochlorite is greater than 9:1.

18. A method as claimed in claim 15, wherein the total chlorine concentration is 250 ppm +/−0% and the starting concentration of the hypochlorous is between 120 and 160 ppm.

19. A method as claimed in claim 15, wherein the total chlorine concentration is 80 ppm +/−20% and the starting concentration of the hypochlorous is above 40 ppm.

20. A method as claimed in claim 15, wherein the hypochlorite salt is sodium hypochlorite.

* * * * *